United States Patent [19]

Lafferty et al.

[11] Patent Number: 5,301,657
[45] Date of Patent: Apr. 12, 1994

[54] SLEEVE FOR MAINTAINING THE STERILITY OF AN ARTHROSCOPIC PROCEDURE

[75] Inventors: W. Michael Lafferty, Leucadia, Calif.; George H. Middle; Algis R. Banys, both of Reno, Nev.; Daniel S. Kline, Carlsbad, Calif.

[73] Assignee: Citation Medical Corporation, Reno, Nev.

[21] Appl. No.: 932,957

[22] Filed: Aug. 21, 1992

Related U.S. Application Data

[63] Continuation-in-part of Ser. No. 650,066, Feb. 4, 1991, Pat. No. 5,188,093.

[51] Int. Cl.⁵ .......................... A61B 1/06; A61B 17/06
[52] U.S. Cl. .......................................... 128/6; 206/438
[58] Field of Search .................. 604/163, 171, 263; 128/4, 6, 856; 433/116; 206/69, 363, 364, 438

[56] References Cited

U.S. PATENT DOCUMENTS

| | | | |
|---|---|---|---|
| 4,253,448 | 3/1981 | Terada | 128/4 |
| 4,522,196 | 6/1985 | Cunningham et al. | 128/4 |
| 4,589,404 | 5/1986 | Barath et al. | 128/6 |
| 4,590,923 | 5/1986 | Watanabe | 128/6 |
| 4,607,622 | 8/1986 | Fritch et al. | 128/6 |
| 4,620,769 | 11/1986 | Tsuno | 350/96.26 |
| 4,736,733 | 4/1988 | Adair | 128/6 |
| 4,754,328 | 6/1988 | Barath et al. | 358/98 |
| 4,755,873 | 7/1988 | Kobayashi | 358/98 |
| 4,757,381 | 7/1988 | Cooper et al. | 433/29 |
| 4,762,120 | 8/1988 | Hussein | 128/6 |
| 4,782,819 | 11/1988 | Adair | 128/6 |
| 4,844,071 | 7/1989 | Chen et al. | 128/6 |
| 4,867,138 | 9/1989 | Kubota et al. | 128/6 |
| 4,878,485 | 11/1989 | Adair | 604/263 |
| 4,914,521 | 4/1990 | Adair | 128/6 |
| 4,920,961 | 5/1990 | Grossi et al. | 606/14 |
| 4,947,245 | 8/1990 | Ogawa et al. | 358/98 |
| 4,974,580 | 12/1990 | Anapliotis | 128/4 |
| 5,005,943 | 4/1991 | Fort | 350/96.26 |
| 5,168,863 | 12/1992 | Kurtzer | 604/171 |
| 5,198,894 | 3/1993 | Hicks | 206/438 |

OTHER PUBLICATIONS

Copy of Color Brochure "Total Control"/Intercom System Four Pages, Published by Vastek, Dayton, Ohio, Undated.

*Primary Examiner*—Gene Mancene
*Assistant Examiner*—Cindy A. Cherichetti
*Attorney, Agent, or Firm*—Nydegger & Associates

[57] ABSTRACT

A disposable sterile sleeve is provided which is removably attachable to a video camera of an arthroscope. The sleeve comprises a flexible elongate tubular shroud and a rigid annular mounting collar. The shroud is open ended with the collar rotatably attached to one open end by a connector member providing independent rotation of the collar relative to the shroud. A pull tab is attached to the opposite open end of the shroud to facilitate extension of the shroud over the camera. The sleeve may be compacted for storage prior to use by tightly scrunching the shroud together, thereby folding it onto itself. To attach the sleeve to the camera, the video camera is inserted through the compacted shroud until it engages the collar. A male thread provided on the camera is threaded into a female thread provided on the collar and the shroud is then extended over the camera by pulling on the tab to draw out the folds in the shroud.

18 Claims, 3 Drawing Sheets

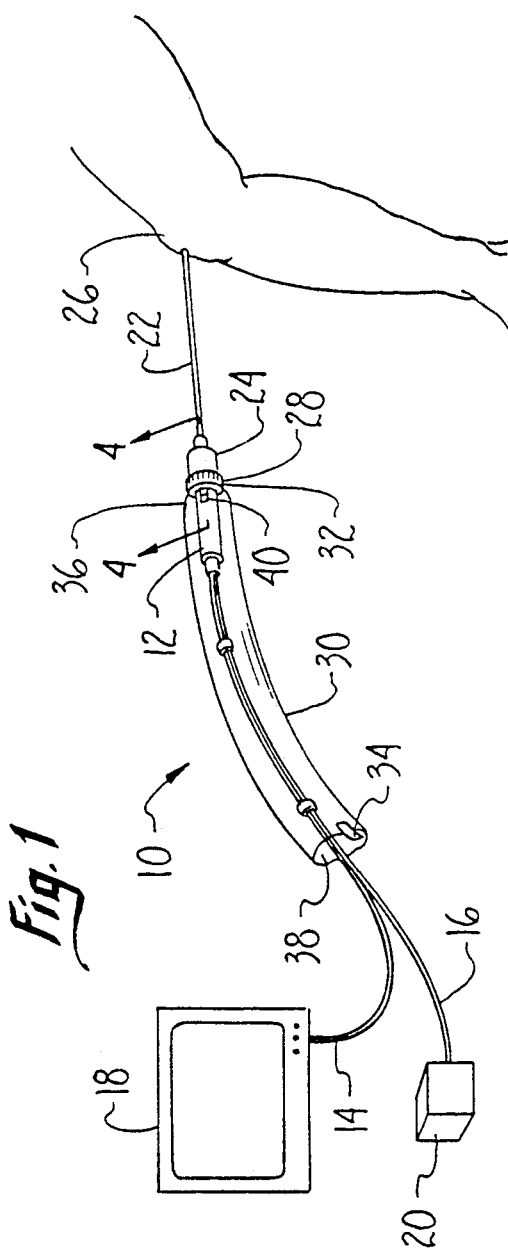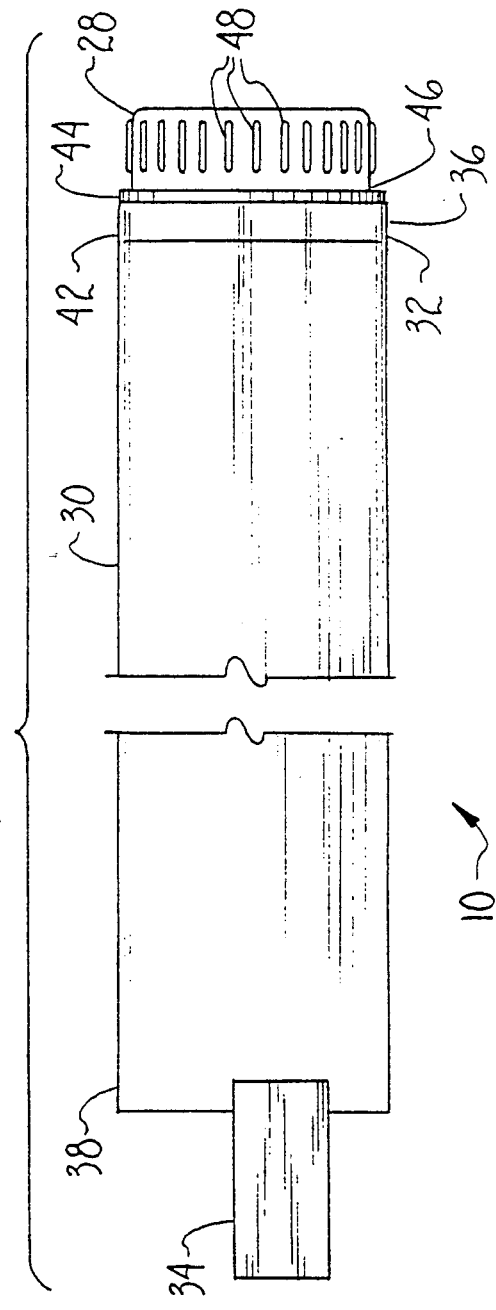

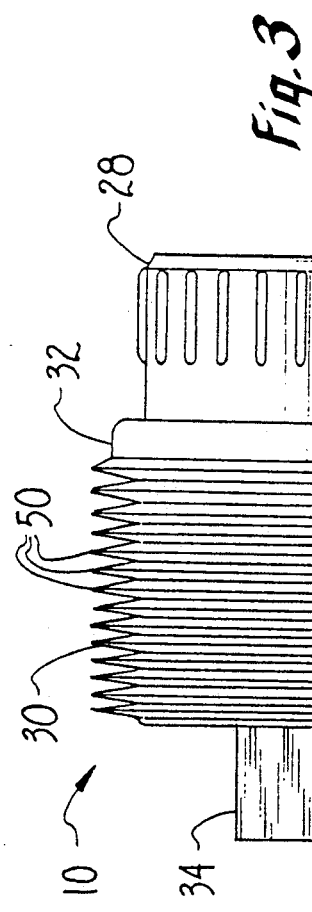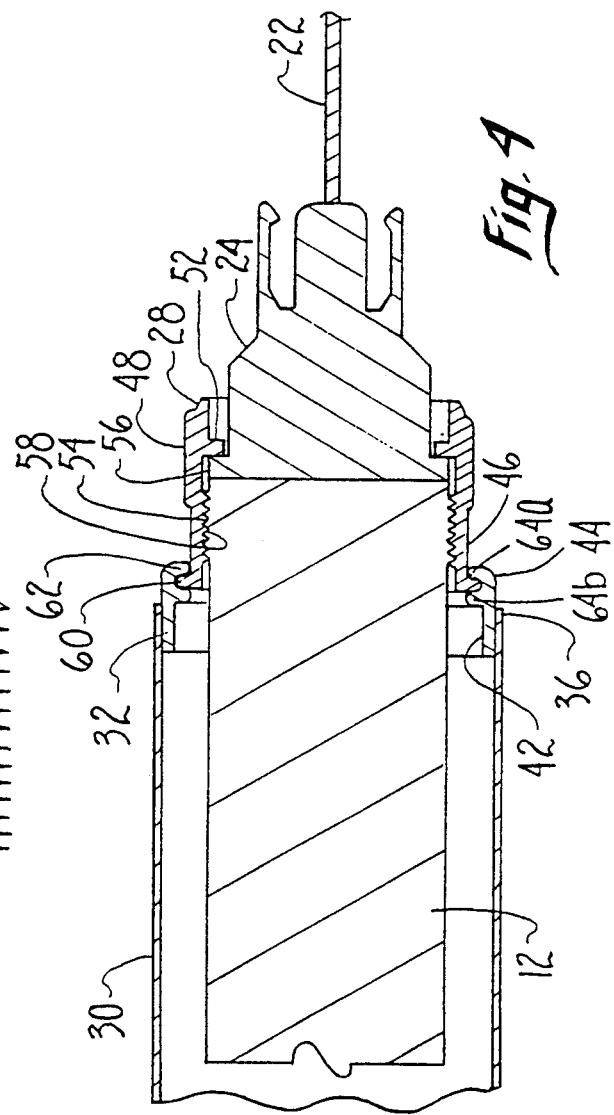

SLEEVE FOR MAINTAINING THE STERILITY OF AN ARTHROSCOPIC PROCEDURE

This is a continuation-in-part patent application of co-pending U.S. patent application Ser. No. 07/650,066 filed on Feb. 4, 1991, now U.S. Pat. No. 5,188,093 and entitled "Portable Arthroscope With Periscope Optics".

FIELD OF THE INVENTION

The present invention relates generally to medical diagnostic devices, and particularly to an accessory for use in conjunction with an arthroscope. The present invention more particularly, though not exclusively, relates to a sterile sleeve for covering certain portions of an arthroscope during an arthroscopic procedure.

BACKGROUND OF THE INVENTION

In the field of medicine, modern techniques have been developed for diagnosing damage to the interior structure of a living body. One such technique is arthroscopy, which is most commonly used to examine the interior structure of bone joints, such as the knee joint, and to determine the existence and extent of any damage in the joint. A significant advantage of arthroscopy is that it permits internal viewing of the body joint without requiring conventional invasive surgery to externally expose the joint. Furthermore, if joint damage is discovered during the examination, relatively non-invasive corrective surgery can be performed in conjunction with the arthroscopic examination thereby repairing the joint damage.

Arthroscopic examination employs a device termed an arthroscope which typically includes a probe, an imaging device and a video display. In operation, the probe is inserted into the joint being examined. The probe is connected to the imaging device which in turn is connected to a video display, thereby generating a picture of the interior structure of the joint. Consequently, the operator of the arthroscope is able to view, real-time, the interior structure of the joint while the probe is in place in the joint. This enables rapid diagnosis of any damage to the joint and the prescription of appropriate treatment.

Despite the relatively non-invasiveness of arthroscopic procedures, insertion of the probe into the patient places the patient at some risk of infection. Accordingly, it is desirable to perform arthroscopic procedures under strict hygienic conditions to minimize this risk. Sterilizing the probe is the most obvious measure for avoiding contamination. This can be accomplished by employing reusable probes which are sterilized before each use. Alternatively and preferably, prepackaged sterile disposable probes can be employed which are discarded after use.

Although it is clearly critical to maintain the sterility of the probe during an arthroscopic procedure, it is also very desirable to prevent contamination by other arthroscope components which may come into contact with the patient or the probe. In particular, it is desirable that the imaging device, which is typically a handheld video camera, and the line feeding the image from the imaging device to the video display be isolated. This is because the camera and line are immediately adjacent to the probe and near the probe's point of entry into the patient. The isolation of these components is of great importance because, unlike the disposable sterile probe, they are reused in subsequent procedures. This unfortunately increases the risk of infection from contamination transmitted from a previous procedure.

As can be appreciated, it is extremely difficult to sterilize sensitive electronic equipment that cannot stand up to the harsh conditions of a sterilization autoclave. Moreover, sterilizing liquids may damage the equipment or may not be totally effective. Accordingly, a need exists for adequate means of performing hygienic arthroscopic procedures. Specifically, a need exists for assuring the sterility of arthroscope components without subjecting them to the harshness of conventional sterilization procedures. Further, a need exists for a cost-effective means of achieving this result.

In light of the above, it is an object of the present invention to provide a disposable sterile barrier for arthroscopic cameras. It is another object of the present invention to provide a barrier which when installed still allows manipulation of the arthroscopic camera controls. Yet another object of the present invention is to provide a barrier which can be used on existing cameras. Still another object of the present invention is to provide a barrier which is easy to install and use and which does not significantly increase preparation times for arthroscopic procedures. And yet another object of the present invention is to provide a barrier which is relatively easy to manufacture and is comparatively economical.

SUMMARY

The device of the present invention is a sterile sleeve which is attachable to a video camera of an arthroscope and which provides a disposable sterile barrier between the patient, the camera and the associated cables. Generally, the sleeve includes an elongated tubular shroud with a slip ring which is attachable to the probe end of the arthroscopic camera. The shroud then extends to completely enclose the camera and a portion of the transmission cables.

More specifically, the shroud is a hollow tube-like member with two open ends. The flexible shroud is a thin lightweight plastic material which allows the surgeon to manipulate the camera controls once the shroud is installed enclosing the camera. One end of the shroud is attached to an annular, relatively rigid slip ring type connecting member. This slip ring is slidably connected to a collar such that the slip ring and the shroud are rotatable relative to the collar during installation and use.

The collar is designed to thread onto the probe end of the camera thereby attaching the sleeve to the camera. The collar, on its inside surface, includes a flange designed to engage a shoulder on a standard disposable probe and to retain the probe in contact with the camera. In effect, the sleeve collar replaces the typical collar used to retain the probe on the camera. Accordingly, for installation, the probe is first placed against the camera and then the sleeve is placed over the probe until the collar threads can be threaded into the camera threads. During threading, the flange on the collar contacts the shoulder on the probe and forces the probe against the camera. In this manner, the probe and the sleeve are fixably attached to the camera.

To complete the sterile barrier, the sleeve needs to be extended to enclose the camera and the cabling. To facilitate the extension process, a tab is attached to the end of the sleeve opposite the slip ring and the collar. Accordingly, the tab can be gripped by the installer and pulled in a direction away from the probe and toward the cables. The tab is pulled until the shroud is fully extended and completely encloses the camera and a portion of the cables.

For storage and installation, the shroud is scrunched up. The resulting compacted sleeve retains its tubular configuration, but is squat rather than elongated, with the collar and pull tab remaining exposed at opposite ends of the sleeve. To prevent contamination of the compacted sleeve during storage and handling prior to use, the sleeve is sealed in a sterile packet. Other sterile disposable components used during the arthroscopic procedure can also be placed within the same packet for the convenience of the medical personnel performing the procedure.

When it is desired to use the sleeve, it is removed from the packaging at the point of use without compromising the sterility of the sleeve. The compacted sleeve is placed over the camera and probe and is installed as described above.

If desired, a stand can be provided to hold the camera while positioning the sleeve over the camera. The stand is a fixed upright tube having an open end to receive the camera and a slot in its side through which the transmission lines extend. The stand enables the operator to place the sleeve over the camera with a minimum of handling to avoid breaching the sterile field. Once the sleeve is properly positioned, the camera is removed from the stand and the shroud is fully extended over the transmission lines.

With the sleeve in position over the camera and lines, the physician can operate the camera across the transparent flexible shroud without hinderance therefrom, while protecting the patient from the unsterilized surface of the camera and line. The sleeve simultaneously protects the camera from any body fluids released during the arthroscopic procedure. Upon completion of the procedure, the sleeve is removed by unscrewing the collar from the camera and pulling the sleeve off of the lines and camera and the sleeve is finally disposed of as medical waste.

Use of the sleeve obviates time-consuming cleaning of the camera after each procedure. Thus, a number of arthroscopic procedures can be hygienically performed in rapid succession using the sterile sleeves of the present invention.

The present invention will be further understood from the accompanying drawings in conjunction with the accompanying description, in which similar reference characters refer to similar parts.

BRIEF DESCRIPTION OF THE DRAWINGS

FIG. 1 is a perspective view of the sterile sleeve of the present invention as used in conjunction with an arthroscope.

FIG. 2 is an elevational view of the sleeve of the present invention in the expanded condition.

FIG. 3 is an elevational view of the sleeve of the present invention in the compacted condition.

FIG. 4 is a partial cross-sectional view of the sleeve of the present invention as seen along line 4—4 in FIG. 1.

DESCRIPTION OF PREFERRED EMBODIMENTS

Figure 5:
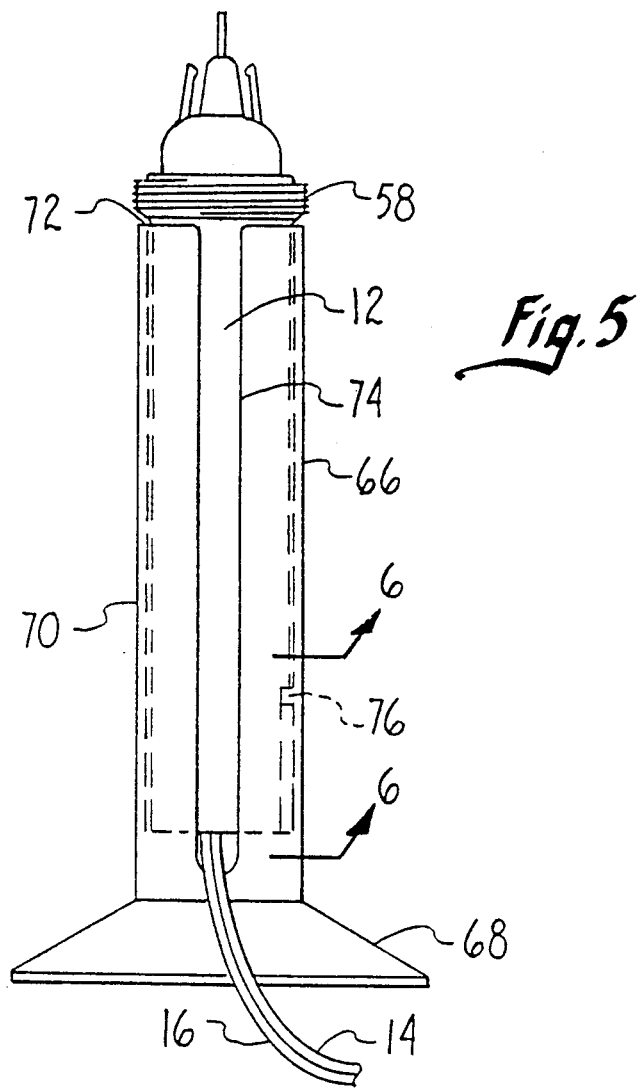
FIG. 5 is a side elevational view of a stand having a video camera positioned therein to receive the sleeve of the present invention.

Referring initially to FIG. 1, a sterile sleeve is shown within its operational environment and generally designated as 10. Sleeve 10 is positioned over video camera 12, as well as a portion of video and illumination lines 14, 16 extending therefrom, during the performance of an arthroscopic procedure. Lines 14 and 16 communicate with a video display 18 and a light box 20, respectively. The arthroscopic procedure further employs a probe 22 mounted on a base 24 that affixes to video camera 12. Probe 22 is inserted into the knee 26 of a patient during performance of the arthroscopic procedure to enable interior viewing thereof.

Sleeve 10 is shown to comprise a collar 28, a shroud 30, a connector member 32 and a pull tab 34. Sleeve 10 is constructed from disposable materials such as plastic or paper. Collar 28 is an annulus preferably formed from a relatively rigid and sturdy plastic. Connector member 32 is likewise an annulus formed from a plastic, although the plastic construction of connector member 32 is somewhat more flexible than collar 28. Connector member 32 may be integrally formed with shroud 30, but in the present preferred embodiment connector member 32 and shroud 30 are shown to be two discrete components of sleeve 10 which are fixably attached. Shroud 30 is an open-ended tubular plastic construct having a proximal end 36 and a distal end 38 relative to collar 28.

Shroud 30 is preferably formed from a highly-flexible plastic sheet that is sufficiently pliable to allow the user to firmly grasp the enshrouded video camera 12 and to manually operate the control mechanisms on camera 12 such as a focusing button 40, across shroud 30. The plastic of shroud 30 is preferably of sufficient strength to resist tearing under normal operating conditions, and is transparent to allow the user visual contact with camera 12 throughout its operation. Pull tab 34 is a strip of disposable tear-resistant material such as plastic or heavyweight paper.

Referring to FIG. 2, assembled sleeve 10 is shown in greater detail. Shroud 30 is an elongate construct that is about 8 to 15 feet in its expanded condition as shown. The interior diameter of expanded shroud 30 is about 1.5 to 3 inches. The interior diameter of connector member 32 is about 1.5 inches or less such that its distal end 42 fits into proximal end 36 of shroud 30. Correspondingly, the interior diameter of collar 28 is somewhat less than that of connector member 32 such that the proximal end 44 of connector member 32 fits over the distal end 46 of collar 28.

Distal end 42 of connector member 32 can be fixably attached to proximal end 36 of shroud 30 by either an adhesive, or thermal bonding, to form a tight seal therebetween. Distal end 46 of collar 28 is rotatably attached to proximal end 44 of connector member 32 in a manner described hereafter such that collar 28 is freely rotatable independent of connector member 32 and shroud 30 to facilitate removable attachment of collar 28 onto video camera 12 in a manner likewise described hereafter. Collar 28 has a plurality of ridges 48 formed thereon which allow the user to firmly grip collar 28 during removable attachment of collar 28 to video camera 12.

Tab 34 is fixably attached to distal end 38 of shroud 30 by means of an adhesive. As shown in FIG. 2, tab 34 is a two-sided rectangular strip of paper tape having the adhesive side doubled over onto itself as well as onto the inner and outer sides of distal end 38, and further having the nonadhesive side exposed to the user.

Assembly of sleeve 10 is preferably facilitated by sliding annular components 28, 30, 32 over a mandrel (not shown) to maintain the components in desired relation to one another until assembly of sleeve 10 is completed. Prior to assembly, shroud 30 is reduced to a compact condition for ease of handling. Compaction further facilitates storage of sleeve 10 and also placement of sleeve 10 over video camera 12 and lines 14 and 16 at the time of use. Compaction is achieved with shroud 30 mounted on the mandrel by tightly scrunching shroud 30 together to produce a plurality of folds 50 along the entire length of shroud 30.

Folds 50 are stabilized by heat treatment, thereby enabling shroud 30 to maintain its compact condition. Heat treatment is performed by inserting the mandrel having shroud 30 positioned thereon into an oven at a predetermined temperature below the melting point of the plastic making up shroud 30, but at a temperature sufficient to deform the plastic thereby diminishing the elastic tension in folds 50. The predetermined temperature is preferably on the order of about 90° C. Sleeve 10 is preferably maintained at the predetermined temperature for a predetermined time on the order of about 10 to 20 minutes.

After heat treatment, the mandrel and shroud 30 are withdrawn from the oven and cooled. Sleeve 10 is then assembled with shroud 30 in a compact condition and the completed assembly is removed from the mandrel for subsequent sterile packaging and storage. Sleeve 10 has a squat configuration in the compact condition shown in FIG. 3, when compared to the elongate expanded condition of sleeve 10 shown in FIGS. 1 and 2. Sleeve 10 in its compact condition remains tubularly configured and has a length on the order of about 3 to 6 inches with collar 28 and tab 34 exposed at opposite ends 36, 38.

In use, sleeve 10 is connected to video camera 12 by means of a collar 28 as shown in detail with reference to FIG. 4. For purposes of clarity, those cross-sectional details of video camera 12, probe 22 and base 24 not necessary for purposes of the teaching of the present invention are not shown herein, but are disclosed with reference to the parent application, U.S. patent application Ser. No. 07/650,066, filed on Feb. 4, 1991 and entitled "Portable Arthroscope With Periscope Optics", which is incorporated herein by reference.

To enable removable mounting of sleeve 10 onto video camera 12, collar 28 is provided with a flange 52 and a female thread 54 on its inside surface which cooperate with a shoulder 56 on base 24 and a male thread 58 on video camera 12. Collar 28 is further provided with an annular rail 60 on the outside surface of its distal end 46 which cooperates with a track 62 formed on the inside surface of the distal end 44 of connector member 32 to retain collar 28 in continuous rotatable engagement with connector member 32.

Mounting of sleeve 10 is performed by inserting distal end 38 of compacted sleeve 10 over probe 22 and base 24 which are connected to camera 12. Sleeve 10 is conveyed along the length of camera 12 until the probe 22 and base 24 extend through the proximal end 36 of sleeve 10 and flange 52 abuts shoulder 56. Simultaneously therewith, male thread 58 on camera 12 engages female thread 54 on collar 28 and male thread 58 is then fully threaded into female thread 54 such that video camera 12 abuts base 24. Threading is facilitated by the rotational independence of collar 28 from connector member 32 and shroud 30 which enables collar 28 to rotate while shroud 30 remains stationary. Rotational independence is provided by the connection of collar 28 and connector member 32 across annular rail 60 and track 62, wherein track 62 has resilient parallel sides 64a, 64b which form an expandable opening to receive rail 60 upon assembly and elastically retain rail 60 thereafter. Mounting is completed by grasping tab 34 and manually drawing it in a distal direction. The pulling force applied to tab 34 functions to extend folds 50 and transform sleeve 10 to the expanded condition to cover video camera 12 and at least partially cover lines 14 and 16.

Figure 6:
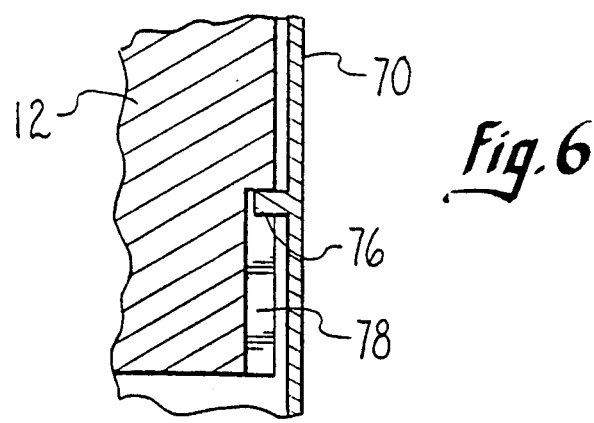
FIG. 6 is a partial cross-sectional view of the stand having the video camera positioned therein as seen along line 6—6 in FIG. 5.

Mounting of sleeve 10 onto video camera 12 may be facilitated by means of a camera stand 66 as shown in FIG. 5. Stand 66 comprises a pedestal 68 which may be stationarily fixed to a free-standing structure such as a cart (not shown). Standing upright atop the pedestal 68 is a tubular member 70 having an open end 72 opposite pedestal 68. Tubular member 70 has a slot 74 formed in its wall which extends downward from open end 72. To use stand 66, the video camera 12 is placed down into tubular member 70 through open end 72 with lines 14, 16 extending through slot 74. A pin 76 is shown, in phantom, positioned within tubular member 70 to engage video camera 12. The function of pin 76 is shown in more detail with reference to FIG. 6, wherein pin 76 engages a pin receiving slot 78 formed in the surface of video camera 12. Pin 76 abuts the edge of slot 78, thereby acting as a stop for camera 12 to maintain threads 58 exposed atop open end 72 and to prevent camera 12 from rotating within stand 66.

Referring back to FIG. 5, it is apparent that with video camera 12 positioned in stand 66, sleeve 10 can be mounted onto camera 12 in the manner described above. Shroud 30 can then be partially extended by feeding it over tubular member 70. Thereafter, camera 12 is removed from stand 66 and shroud 30 is fully extended over lines 14, 16. The stand 66 minimizes the handling of camera 12, thus, reducing the risk of breaching the sterile field.

While the particular sleeve for maintaining the sterility of an arthroscopic procedure as herein shown and disclosed in detail is fully capable of obtaining the objects and providing the advantages hereinbefore stated, it is to be understood that the sleeve is merely illustrative of the presently preferred embodiments of the invention and that other embodiments are possible within the scope of the present invention.

We claim:

1. A device for maintaining the sterility of an arthroscopic video camera comprising:
   a thread on said video camera;
   a flexible elongated shroud having a hollow tubular configuration with an open proximal end and an open distal end;
   an annular collar connected to said open proximal end of said shroud, said collar having a thread engagable with said thread on said video camera, wherein said shroud is extendable over the length of said video camera when said collar threadably engages said video camera; and
   a means for rotatably retaining said collar in connection with said shroud such that said collar is rotatable independently of said shroud.

2. A device for maintaining the sterility of an arthroscopic video camera as recited in claim 1 further comprising a means for rotatably retaining said collar in connection with said shroud such that said collar is rotatable independent of said shroud.

3. A device for maintaining the sterility of an arthroscopic video camera as recited in claim 2 wherein said retention means comprises an annular rail on said collar and an annular track connected to said proximal end of said shroud, said track having a pair of sides defining an opening to slidably retain said rail.

4. A device for maintaining the sterility of an arthroscopic video camera as recited in claim 3 further comprising a connector member fixably attached to said proximal end of said shroud and having said annular rail mounted thereon.

5. A device for maintaining the sterility of an arthroscopic video camera as recited in claim 4 wherein said connector member is less flexible than said shroud.

6. A device for maintaining the sterility of an arthroscopic video camera as recited in claim 4 wherein said collar is rigid relative to said shroud and said connector member.

7. A device for maintaining the sterility of an arthroscopic video camera as recited in claim 3 wherein said retention means comprises an annular track on said collar and an annular rail connected to said proximal end of said shroud, said track having a pair of sides defining an opening to slidably retain said rail.

8. A device for maintaining the sterility of an arthroscopic video camera as recited in claim 1 wherein said shroud has an expanded condition in which said shroud covers said video camera, and a compact condition, and further wherein said shroud defines a plurality of folds therein when in said compact condition.

9. A device for maintaining the sterility of an arthroscopic video camera as recited in claim 8 further comprising a means for receiving a force and transmitting said force to said distal end of said shroud for unfolding said folds, thereby transforming said shroud from said compact condition to said expanded condition.

10. A device for maintaining the sterility of an arthroscopic video camera as recited in claim 9 wherein said receiving means is a tab fixably attached to said distal end of said shroud.

11. A device for maintaining the sterility of an arthroscopic video camera comprising:
a male thread on said video camera;
a flexible elongated shroud having a hollow tubular configuration with an open proximal end and an open distal end; and
an annular collar connected to said open proximal end of said shroud, said collar threadably engagable with said video camera, wherein said shroud is extendable over the length of said video camera when said collar threadably engages said video camera, and wherein said collar has a female thread engagable with said male thread on said video camera.

12. A device for maintaining the sterility of an arthroscopic video camera comprising:
a flexible elongated shroud having a tubular configuration with an open proximal end and an open distal end;
an annular collar connected to said open proximal end of said shroud, wherein said collar is engageable with said video camera, and further wherein said shroud is extendable over said video camera when said collar engages said video camera;
a means for connecting said collar with said shroud wherein said connecting means allows said collar to rotate relative to said shroud; and
a means for receiving a force and transmitting said force to said distal end of said shroud for unfolding said shroud, said shroud enclosing said camera to provide a sterile barrier between said camera and a patient.

13. A device for maintaining the sterility of an arthroscopic video camera and a transmission line extending therefrom comprising:
an upright tubular member having an open end to receive said video camera therein, while maintaining a thread on said camera exposed, said tubular member further having a slot formed in its side through which said transmission line extends;
a flexible elongated shroud having a tubular configuration with an open proximal end and an open distal end, wherein said shroud has an expanded condition and a compact condition, and further wherein said shroud defines a plurality of folds therein when in said compact condition;
an annular collar connected to said open proximal end of said shroud, said collar having a thread engageable with said thread on said video camera, said shroud extending over said video camera.

14. A device for maintaining the sterility of an arthroscopic video camera as recited in claim 13 further comprising a pin attached to the interior of said tubular member, wherein said pin is sized to be receivable by a slot formed on the surface of said video camera, thereby preventing rotation of said video camera when positioned in said tubular member.

15. A method for maintaining the sterility of an arthroscopic video camera comprising the steps of:
placing a probe on said camera;
conveying a barrier member along said probe until a collar attached to said barrier member contacts said camera;
fastening said collar to said video camera, said collar being connected to a shroud having an open distal end, said shroud having an expanded condition and compacted condition; and
extending said shroud by moving said open distal end over said video camera and at least one transmission line connected to said video camera.

16. The method of claim 15 wherein said extending step further comprises applying a force to a tab attached to said open distal end until said shroud is in said expanded condition.

17. The method of claim 16 wherein said fastening step further comprises rotating said collar to engage threads on said collar with threads on said video camera, said connection between said collar and said shroud allowing said collar to rotate independently of said shroud.

18. The method of claim 17 further comprising the step of placing said video camera in an upright tubular member having an open end to receive said video camera therein, said tubular member further having a slot formed in its side through which said transmission line extends.

* * * * *